(12) United States Patent
Boele et al.

(10) Patent No.: US 7,504,545 B2
(45) Date of Patent: Mar. 17, 2009

(54) PROCESS FOR THE PREPARATION OF ALKYLENE GLYCOLS

(75) Inventors: Dirk Michiel Boele, Amsterdam (NL); Henricus Petrus Bernardus Duijghuisen, Amsterdam (NL); Eugene Marie Godfried Andre Van Kruchten, Amsterdam (NL); Jan Hermen Hendrik Meurs, Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 11/855,609

(22) Filed: Sep. 14, 2007

(65) Prior Publication Data

US 2008/0139853 A1    Jun. 12, 2008

(30) Foreign Application Priority Data

Sep. 15, 2006   (EP)   .................. 06254818

(51) Int. Cl.
*C07C 29/10*   (2006.01)

(52) U.S. Cl. .................................... 568/867
(58) Field of Classification Search ................ 568/867
See application file for complete search history.

(56) References Cited

U.S. PATENT DOCUMENTS

| 2,993,908 A | 7/1961 | Millikan | 260/340.2 |
|---|---|---|---|
| 3,535,341 A | 10/1970 | Emmons | 260/340.2 |
| 3,535,342 A | 10/1970 | Emmons | 260/340.2 |
| 4,160,116 A | 7/1979 | Mieno et al. | 568/867 |
| 4,283,580 A | 8/1981 | Odanaka et al. | 568/858 |
| 4,307,256 A | 12/1981 | Cipriani et al. | 568/867 |
| 4,314,945 A | 2/1982 | McMullen et al. | 260/340.2 |
| 4,778,658 A | 10/1988 | Nielsen | 422/111 |
| 4,786,741 A | 11/1988 | Sachs | 549/230 |
| 4,982,021 A | 1/1991 | Best et al. | 568/867 |
| 5,218,135 A | 6/1993 | Buysch et al. | 558/277 |
| 5,391,767 A | 2/1995 | Mais et al. | 549/229 |
| 5,488,184 A | 1/1996 | Reman et al. | 568/867 |
| 6,124,508 A | 9/2000 | Van Kruchten | 568/867 |
| 6,153,801 A | 11/2000 | Van Kruchten | 568/867 |
| 6,156,909 A | 12/2000 | Kim et al. | 549/230 |
| 6,160,130 A | 12/2000 | Kim et al. | 549/230 |
| 6,399,536 B2 | 6/2002 | Kim et al. | 502/169 |

FOREIGN PATENT DOCUMENTS

| DE | 1543555 | 3/1975 |
|---|---|---|
| EP | 156449 | 10/1985 |
| EP | 776890 | 1/2001 |
| EP | 1034158 | 8/2003 |
| FR | 2644795 | 9/1990 |
| GB | 2085748 | 5/1982 |
| JP | 56092228 | 7/1981 |
| JP | 57106631 | 7/1982 |
| JP | 59013741 | 1/1984 |
| JP | 2001151711 | 6/2001 |
| JP | 2001151713 | 6/2001 |
| WO | WO9520559 | 8/1995 |
| WO | WO2005003113 | 1/2005 |

OTHER PUBLICATIONS

J. Catal (2002) 205, 226-229.
J. Catal (2003) 220, pp. 44-46.
Angew. Chem. Int Ed (2000) 39 (227), pp. 4096-4098.
Chem. Eur. J. (2003) 9(3), pp. 678-686.
Chem. Ber. (1986) 119, pp. 1090-1094.
Appl. Catal., A (2005) 275-pp. 125-129.
Chem. Commun (2006), pp. 1664-1666.
Kirk Othemer's Encyclopedia of Chemical Technology, 4th Edition, vol. 9, pp. 923-940 , (1992).

*Primary Examiner*—Sikarl A Witherspoon

(57) ABSTRACT

A process for the conversion of an alkylene oxide to the corresponding alkylene glycol in the presence of carbon dioxide, water and a catalytic composition comprising a mixture of an organic base present in an amount in the range of from 10 to 90 mol % (based on the mixture) and a salt of the organic base and a hydrogen halide the salt being present in an amount in the range of from 10 to 90 mol % (based on the mixture), wherein the organic base comprises a carbon-based compound comprising one or more nitrogen atoms with at least one free electron pair and/or one or more phosphorous atoms with at least one free electron pair, and has a pKa high enough that it is capable of binding carbon dioxide under the reaction conditions.

20 Claims, No Drawings

PROCESS FOR THE PREPARATION OF ALKYLENE GLYCOLS

CROSS-REFERENCE TO RELATED APPLICATIONS

This application claims the benefit of European Patent Application No. 06254818.5, filed Sep. 15, 2006, which is incorporated herein by reference in its entirety.

FIELD OF THE INVENTION

The invention relates to a process for the catalytic conversion of alkylene oxide to alkylene glycols.

BACKGROUND OF THE INVENTION

Alkylene glycols, in particular monoalkylene glycols, are of established commercial interest. For example, monoalkylene glycols are used in anti-freeze compositions, as solvents and as base materials in the production of polyalkylene terephthalates e.g. for fibres or bottles.

The production of alkylene glycols by liquid phase hydrolysis of alkylene oxide is known. The hydrolysis is generally performed by adding a large excess of water, e.g. 20 to 25 moles of water per mole of alkylene oxide. The reaction is considered to be a nucleophilic substitution reaction, whereby opening of the alkylene oxide ring occurs, water acting as the nucleophile. Because the primarily formed monoalkylene glycol also acts as a nucleophile, as a rule a mixture of monoalkylene glycol, dialkylene glycol and higher alkylene glycols is formed. In order to increase the selectivity to monoalkylene glycol, it is necessary to suppress the secondary reaction between the primary product and the alkylene oxide, which competes with the hydrolysis of the alkylene oxide.

One effective means for suppressing the secondary reaction is to increase the relative amount of water present in the reaction mixture. Although this measure improves the selectivity towards the production of the monoalkylene glycol, it creates a problem in that large amounts of water have to be removed for recovering the product.

Considerable efforts have been made to find an alternative means for increasing the reaction selectivity without having to use a large excess of water. The hydrolysis of alkylene oxides to alkylene glycols can be performed with a smaller excess of water in a catalytic system. Therefore, these efforts have usually focused on the selection of more active hydrolysis catalysts and various catalysts have been disclosed in the literature.

Catalytic processes, promoting a higher selectivity to monoalkylene glycol product at reduced water levels are known (e.g. EP-A-0,156,449, U.S. Pat. No. 4,982,021, U.S. Pat. No. 5,488,184, U.S. Pat. No. 6,153,801 and U.S. Pat. No. 6,124,508). Such catalysts often comprise a strongly basic (anionic) exchange resin, often with quaternary ammonium or quaternary phosphonium electropositive complexing sites, coordinated with one or more anions (e.g. metalate, halogen, bicarbonate, bisulfite or carboxylate).

Further examples of catalytic processes known for the reaction of alkylene oxides to alkylene glycols are given in JP 2001151713 and JP 2001151711, wherein a catalytic composition comprising a halide ion and a bicarbonate ion is used to convert an alkylene oxide to the corresponding alkylene glycol in the presence of carbon dioxide and water.

JP-A-56,092,228 is directed to the use of molybdenum and/or tungsten as a catalyst for the conversion of alkylene oxide to alkylene glycol, again in the presence of carbon dioxide and water.

U.S. Pat. No. 4,307,256 describes the reaction of alkylene oxides with water and carbon dioxide in the presence of a tertiary amine catalyst for the production of alkylene glycols. In U.S. Pat. No. 4,160,116 a similar system is described, wherein the catalyst used is a quaternary phosphonium salt.

EP-A-1,034,158 is directed to the use of a catalytic composition comprising a macrocyclic chelating compound complexed with an ionic compound selected from the group comprising halogenides, carboxylates, hydrogen carbonates, hydrogen sulphites, hydrogen phosphates, and metalates, for the hydrolysis of alkylene oxides to alkylene glycols.

In addition, processes for the production of alkylene glycols from alkylene oxides, comprising a two-step process, have been described in the art. Such processes involve the reaction of alkylene oxides with carbon dioxide in the presence of a catalyst, followed by subsequent thermal or catalytic hydrolysis of the resultant alkylene carbonate. Examples of such two-step processes include those described in JP-A-57,106,631 and JP-A-59,013,741.

Catalysts suitable for the hydrolysis of alkylene carbonates are described in U.S. Pat. No. 4,283,580, which is directed to the use of molybdenum or tungsten in metal or compound form as catalysts in the production of substituted or unsubstituted ethylene glycols by the reaction of substituted or unsubstituted ethylene carbonates with water.

The application of acid salts of hydrazine and guanidine as catalysts for the reaction of an alkylene oxide with $CO_2$ under superatmospheric pressure, to form an alkylene carbonate, is described in U.S. Pat. No. 3,535,341 and U.S. Pat. No. 3,535,342, respectively. Halide salts of ureas have also been reported as catalysts for this reaction in U.S. Pat. No. 2,993,908. DE-A-1,543,555 teaches the uses of derivatives of carbamic acids, particularly the stable salts of the basic derivatives of carbamic acids, for the conversion of alkylene oxide to alkylene carbonate.

Although progress has been made in developing catalyst systems for the conversion of alkylene oxide to alkylene glycols, the need for new processes with high levels of conversion using highly active and selective catalyst compositions prepared from readily available materials still remains. Further, catalysts capable of being used in a heterogeneous system and thus allowing facile separation of the product alkylene glycols from the catalyst are also desired.

SUMMARY OF THE INVENTION

The present invention provides a process for the conversion of an alkylene oxide to the corresponding alkylene glycol in the presence of carbon dioxide, water and a catalytic composition comprising a mixture of in the range of from 10 to 90 mol % (based on the mixture) of an organic base and in the range of from 10 to 90 mol % (based on the mixture) of the salt of the organic base and a hydrogen halide, wherein the organic base comprises a carbon-based compound comprising one or more nitrogen atoms with at least one free electron pair and/or one or more phosphorous atoms with at least one free electron pair, and has a pKa high enough that it is capable of binding carbon dioxide under the reaction conditions.

DETAILED DESCRIPTION OF THE INVENTION

We have surprisingly found that alkylene glycols may be obtained with excellent activity and/or selectivity by reaction of the corresponding alkylene oxide in the presence of water, carbon dioxide and a catalytic composition comprising a mixture of a free organic base and a salt formed by the neutralisation of the organic base with a hydrogen halide, wherein the molar ratio of the free organic base to the salt is in the range of from 1:9 to 9:1 and the organic base comprises a carbon-based compound containing one or more nitrogen atoms with at least one free electron pair and/or one or more phosphorous atoms with at least one free electron pair, and wherein the organic base has a pKa high enough that it is capable of binding carbon dioxide under the reaction conditions.

The alkylene oxide used as starting material in the process of the invention has its conventional definition, i.e. it is a compound having a vicinal oxide (epoxy) group in its molecules.

Particularly suitable are alkylene oxides of the general formula (I),

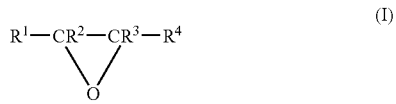

wherein $R^1$ to $R^4$ independently represent a hydrogen atom or an optionally substituted, alkyl group having from 1 to 6 carbon atoms. Any alkyl group, represented by $R^1$, $R^2$, $R^3$ and/or $R^4$ preferably has from 1 to 3 carbon atoms. As substituents, inactive moieties, such as hydroxy groups may be present. Preferably, $R^1$, $R^2$ and $R^3$ represent hydrogen atoms and $R^4$ represents a non-substituted $C_1$-$C_3$-alkyl group and, more preferably, $R^1$, $R^2$, $R^3$ and $R^4$ all represent hydrogen atoms.

Examples of suitable alkylene oxides therefore include ethylene oxide, propylene oxide, 1,2-epoxybutane and 2,3-epoxybutane. In the present invention, the most preferred alkylene oxide is ethylene oxide.

The preparation of alkylene oxides is well known to the skilled person. In the case of ethylene oxide, it may be prepared by the well known direct oxidation of ethylene, i.e. by air or oxygen oxidation, utilizing silver-based catalysts and often also organic moderators, e.g. organic halides (see for example Kirk Othmer's Encyclopedia of Chemical Technology, $4^{th}$ edition, Vol. 9, pages 923-940).

Organic bases, according to the present invention, are carbon-based compounds also containing one or more nitrogen and/or phosphorous atoms which have at least one free electron pair. To be effective in the present invention, the organic base should have a pKa high enough such that it is capable of binding carbon dioxide under the reaction conditions. Preferably, the pKa of the organic base should be at least 8, more preferably at least 13. Suitable organic bases include, but are not limited to, amines, hydroxylamines, hydrazines, hydrazones, amidines, amidrazones, hydrazidines, formazans, carbodiimides, guanidines, ureas, cyanamides, pyridines, pyrimidines, quinolines, imidazoles, triazoles, phosphazenes, phosphines, imines, and imides, having a pKa high enough that it is capable of binding carbon dioxide under the reaction conditions. Preferably, the organic base is selected from the group comprising phosphazenes, amines, pyridines, and guanidines.

Preferably, the hydrogen halide used to form a salt with the organic base is selected from hydrogen fluoride, hydrogen chloride, hydrogen bromide, and hydrogen iodide. Most preferably, the hydrogen halide is hydrogen iodide.

In a preferred embodiment of the present invention, the organic base is immobilised on a solid support. Thus, in this embodiment, the catalytic composition will comprise a mixture of in the range of from 10 to 90 mol % (based on the mixture) of the free base immobilised on a solid support and from 10 to 90 mol % (based on the mixture) of the salt of the solid-supported organic base and a hydrogen halide. Typically, in this embodiment, the organic base will be immobilised on the solid support before reaction with the hydrogen halide.

Solid supports suitable for use in the process of the present invention include those of an inorganic nature such as carbon, silica, silica-alumina, zeolites, glass and clays. Such solid supports may have the organic base bonded by adsorption, reaction or grafting. Advantageously, in the present invention, solid supports comprising a polymeric backbone are used. The polymeric backbone may comprise high molecular weight polymers and co-polymers including polyalkylene, polyester, polycarbonate, polyurethane, formaldehyde resins, etc. Silica-based polymeric backbones, such as polysiloxanes may also be used. Weakly basic ion exchange resins, for example REILLEX 402 (polyvinylpyridine), are also suitable (REILLEX is a trade mark).

The mixture of the free organic base and the salt of the organic base and a hydrogen halide may be formed as a physical mixture of in the range of from 10 to 90 mol %, preferably in the range of from 20 to 80 mol %, (based on the mixture) of the free organic base mixed with in the range of from 10 to 90 mol %, preferably in the range of from 20 to 80 mol %, (based on the mixture) of the pre-formed salt of the organic base and the hydrogen halide.

The salt of the organic base and the hydrogen halide may be formed by any specific method known in the art which involves reacting the free organic base and hydrogen halide together in amounts relative to each other such that an aqueous solution of the product formed has a pH in the range of from 6 to 8, preferably in the range of from 6.5 to 7.5, most preferably in the range of from 6.9 to 7.1. The pH of such a solution can be measured by any of the methods well known in the art, such as by using a standard pH meter or indicator paper.

In the case of solid supported organic bases, wherein an aqueous solution of the base cannot be formed, sufficient hydrogen halide should be added to the solid supported base in water so that the hydrogen halide is present in at least a 1:1 ratio of hydrogen halide to the number of basic centres present in the supported organic base. The number of basic centres present in a specific amount of a particular solid-supported organic base can easily be calculated by one skilled in the art based on the number of basic centres in an individual molecule of the organic base, the density of the organic base molecules on the solid support and the amount of the solid-supported organic base compound used. If too much hydrogen halide is added, the pH of the aqueous solution surrounding the solid catalyst will fall below 6. Excess hydrogen halide can then be washed away by repeatedly washing the catalytic composition with deionised water until the wash water has a pH in the range of from 6 to 8, preferably in the range of from 6.5 to 7.5.

Alternatively, the mixture of the free organic base and the salt of the organic base and a hydrogen halide may be formed by reacting a suitable amount of the free organic base with the hydrogen halide such that the resultant mixture comprises in the range of from 10 to 90 mol % (based on the mixture) of an organic base and in the range of from 10 to 90 mol % (based on the mixture) of the salt of the organic base and the hydrogen halide. That is, adding the hydrogen halide to the organic base in a molar ratio of hydrogen halide to the organic base in the range of from 1:10 to 9:10, preferably in the range of from 1:5 to 4:5.

Such reaction of the organic base and the hydrogen halide may be carried out in the reactor before the addition of the alkylene oxide or, alternatively, it may be carried out before addition of the catalytic composition to the reactor.

The amount of water present is usually at least 0.2 mol/mol alkylene oxide present in the reaction mixture, preferably at least 0.5 mol/mol alkylene oxide. An amount of water present of at least 1 mol/mol alkylene oxide is most preferred. Preferably, the amount of water present is less than 25 mol/mol alkylene oxide, more preferably less than 15 mol/mol alkylene oxide. An amount of water present of at most 5 mol/mol alkylene oxide is most preferred.

A benefit of the present invention is that it is possible to carry out the process with high levels of activity and selectivity in the presence of a close to stoichiometric amount of water with respect to alkylene oxide, for example with an amount of water in the range of from 1 mol/mol alkylene oxide to 1.3 mol/mol alkylene oxide, especially with an amount of water of 1 mol/mol alkylene oxide or 1.1 mol/mol alkylene oxide. This reduces the amount of energy required for the removal of excess water from the reaction product.

The water present in the reaction mixture of the present invention may be added to the reaction mixture separately from the alkylene oxide. Alternatively, the alkylene oxide and water may be pre-mixed before being supplied to the reactor. In a preferred embodiment of the invention, an alkylene oxide product mixture from an alkylene oxide reactor is used either without further process steps or after some concentration in a stripper. Most preferably, an ethylene oxide/water mixture, formed by absorption of the product stream from a direct oxidation ethylene oxide reactor is used. This method has a further benefit that the energy expended in isolating the alkylene oxide, prior to the process of the invention, is reduced.

The process of the present invention may be carried out in any suitable solvent known in the art. Suitable solvents include organic solvents such as alkylene carbonates. Preferably the process of the present invention is carried out in water.

Preferably, the total amount of carbon dioxide supplied to the reactor is in an amount of at least 0.1 mol/mol alkylene oxide, more preferably at least 0.5 mol/mol alkylene oxide. Preferably the total amount of carbon dioxide supplied to the reactor is an amount of at most 100 mol/mol alkylene oxide, more preferably an amount of at most 10 mol/mol alkylene oxide.

It is believed, without wishing to be bound by any theory, that a reaction between the free organic base, carbon dioxide and water present in the reaction mixture results in the presence in the reaction mixture of the carbonate salt of the base which can then act as a hydrolysis catalyst. This hydrolysis catalyst allows the conversion of alkylene carbonate, formed by the reaction of the alkylene oxide with carbon dioxide in the presence of the salt of the organic base and a hydrogen halide, to the product alkylene glycol.

Alternatively, in order to provide a more active hydrolysis catalyst, a metallic acid may be reacted with the free organic base present in the catalyst composition, such that a metallate salt is formed instead of the carbonate. Preferably, the metallic acid is molybdic acid and the salt formed is the molybdate salt of the organic base. The metallic acid may be added to the organic base in an at most stoichiometric amount with respect to the free organic base in situ once the mixture of the free organic base and the salt of the organic base and the hydrogen halide has been formed. Alternatively, the metallate salt of the organic base may be formed separately and added to the salt of the organic base and the hydrogen halide which has also been formed separately.

The process of the present invention may be carried out in batch operation. However, in particular for large-scale embodiments, it is preferred to operate the process continuously.

When using an immobilised catalyst, such continuous process can be carried out in fixed bed reactors, operated in up-flow or down-flow. Other reactor options include bubble column reactors (suitable for use with both immobilised and homogeneous catalysts) and fluidized bed reactors (suitable for use with immobilised catalysts).

The reactors of the present invention may be maintained under isothermal, adiabatic or hybrid conditions. Isothermal reactors are generally shell- and tube reactors, mostly of the multi-tubular type, wherein a coolant passes outside the tubes and the tubes contain either a reaction mixture including a homogeneous catalyst, or a reaction mixture, which passes over an immobilised catalyst that is retained inside the tubes. Adiabatic reactors are not cooled, and the product stream leaving them may be cooled in a separate heat exchanger.

It may be advantageous for the process of this invention to recycle a part of the reactor output to at least one inlet of the same reactor, because any temperature difference that may arise between the top and the bottom of the reactor is minimised. Accordingly, less external temperature control is required to maintain the reaction temperature than with a conventional reactor. This is particularly advantageous when isothermal conditions are preferred. The part of the reactor output to be recycled may be conveniently separated from the part not to be recycled after the reactor output has left the reactor; or alternatively the part of the reactor output to be recycled may be conveniently removed from the reactor via a different outlet of the reactor than that from which the part of the reactor output not to be recycled is removed. The amount of reactor output mixture to be recycled may be varied to obtain optimum performance with regard to other reaction parameters employed.

In order to accommodate any swelling of the catalyst that may occur during operation when using an immobilised catalyst, the reactor volume can advantageously be greater than the volume occupied by the catalyst therein, for example 10 to 70 vol % greater.

Suitable reaction temperatures for the catalytic preparation of alkylene glycols, according to the current invention, are generally in the range of from 40 to 200° C., whereby temperatures in the range of from 50 to 120° C. are preferred.

The reaction pressure is usually selected in the range of from 100 to 5000 $kP_a$, preferably in the range of from 200 to 3000 $kP_a$, most preferably in the range of from 500 to 2000 $kP_a$.

In one embodiment of the present invention, after the alkylene oxide has been in contact with the catalyst composition in the presence of carbon dioxide and water for a period of time such that greater than 90% of the alkylene oxide has been converted, the reaction temperature is increased by at least 10° C., preferably by at least 20° C. Suitably, the reaction temperature is increased by no more than 60° C., preferably no more than 50° C. In a batch operation, this may be achieved by increasing the temperature of the entire reactor contents. If the reaction is being carried out as a continuous process, the reaction mixture may be fed to a different part of the same reactor, or alternatively to a different reactor, that is operating at the higher temperature.

A problem, which may occasionally arise in certain processes using nitrogen- and or phosphorous-containing catalytic compositions, is the presence of small amounts of amines and/or phosphines as impurities in the product stream. It has been found that during operation, small amounts of amines and/or phosphines may leach from immobilised catalysts into the product stream. When a homogeneous catalyst composition is used, amines and/or phosphines may also remain in the product stream after removal of the catalyst. Besides, amines in the product stream may also originate from corrosion inhibitors, which may be added to the water used in the process. Although the amounts of such amine and/or phosphine contaminants reaching the end-product are generally very small, they may affect the quality of the end-product such that it may be desirable to reduce the amounts to as low as possible so as not to affect the quality of the product. For example, trimethylamine (TMA) and/or dimethylamine (DMA) may reach the end product in an amount of up to 10 ppm while the fishy odour of TMA may be detected in an amount as low as 1 ppb.

An effective measure in removing such amines and/or phosphines is the use of a post-reactor bed, containing an acidic species, particularly a strongly acidic ion exchange resin, which effectively captures the amines and/or phosphines. When using an immobilised homogeneous catalyst, such a post-reactor bed may be positioned directly after the reactor bed. However, when using a non-immobilised, homogeneous catalyst, the post-reactor bed should be used to treat the product stream after removal of the homogeneous catalyst. Strongly acidic ion exchange resins may be of the sulfonic type. Commercially available examples are those known by the trademarks AMBERLYST 15, AMBERJET 1500H, AMBERJET 1200H, DOWEX MSC-1, DOWEX 50W, DIANON SK1B, LEWATIT VP OC 1812, LEWATIT S 100 MB, and LEWATIT S 100 G1. Such strongly acidic ion exchange resins are available in $H^+$ form and in salt form, such as the $Na^+$ form. When only the $H^+$ form of the strongly acidic resin is used in the post-reactor guard bed, the product stream after passing it may become acidic. Using a mixture of the strongly acidic ion exchange resin in its $H^+$ form and salt form has the advantage of the pH of the product stream remaining close to neutral.

An added advantage of the strongly acidic post-reactor bed positioned after the reactor bed in which the alkylene glycol is formed is that any remaining alkylene oxide or alkylene carbonate, which may be still present in the product alkylene glycol product stream, may be hydrolysed to alkylene glycol.

In order to allow for exhaustion of the strongly acidic ion exchange resin during operation, it is advantageous to operate the post-reactor bed in two or more separate vessels, to allow the process to be switched between the two vessels, thus maintaining continuous operation.

Exhausted strongly acidic ion exchange resin can be regenerated by treatment with an acid, such as HCl and $H_2SO_4$. Hot sulfuric acid of 0.1 to 2 N has been proven to be effective.

Having generally described the invention, a further understanding may be obtained by reference to the following examples, which are provided for purposes of illustration only and are not intended to be limiting unless otherwise specified. The following Examples will illustrate the invention.

EXAMPLES

The abbreviations used herein have the following definitions:

| TMG | 1,1,3,3-tetramethylguanidine |
| --- | --- |
| P1 | 2-tert-butylimino-2-diethylamino-1,3-dimethyl-perhydro-1,3,2-diazaphosphorin (a phosphazine) |
| TEA | Tri-ethanolamine |
| P1-POL | 2-tert-butylimino-2-diethylamino-1,3-dimethyl-perhydro-1,3,2-diazaphosphorin on polystyrene |
| TBPMI | methyltributylphosphonium iodide |

The catalyst compositions were produced using the following methods:

Catalyst 1

TMG/TMG-hydroiodide 1,1,3,3-tetramethylguanidine (1.21 g, 10 mmol) was dissolved in approximately 15 g of water. A solution (57 wt %) of hydroiodic acid (1.85 g, 8.2 mmol) was added slowly. The pH was measured as approximately 12.9 and a further 7 g of water was added in order to provide a catalyst solution (0.33 M based on iodide and 0.09M based on free organic base).

Catalyst 2

P1/P1-hydroiodide 2-tert-butylimino-2-diethylamino-1,3-dimethyl-perhydro-1,3,2-diazaphosphorin (2.93 g, 10.7 mmol) was dissolved in approximately 15 g of water. A solution (57 wt %) of hydroiodic acid (1.95 g, 8.8 mmol) was added slowly. The pH of the solution was measured as approximately 13.2 and a further 5.6 g of water was added in order to provide a catalyst solution (0.33M based on iodide and 0.1M based on free organic base).

Catalyst 3

P1-POL/P1-POL-hydroiodide 2-tert-butylimino-2-diethylamino-1,3-dimethyl-perhydro-1,3,2-diazaphosphorin on polystyrene (4.7 g, 2.2 mmol base/g) was combined with approximately 15 g of water. A solution (57 wt %) of hydroiodic acid (1.88 g, 8.4 mmol) was added slowly. The pH of the solution was measured as 11.8 and a further 4 g of water was added in order to provide a catalyst composition (0.34M based on iodide and 0.08M based on free organic base).

The Examples were all carried out in a 125 ml Medimex autoclave according to the following procedures. TBPMI (methyltributylphosphonium iodide) in combination with $K_2CO_3$ was used as a comparative catalyst.

General Reaction Procedure

The reactor was filled with the catalyst composition in water, prepared as stated above. The reactor was then purged with $CO_2$ and pressurised with a $CO_2$ atmosphere of approximately 5 bar (500 $kP_a$). The reactor content was then heated to 90° C. and the reactor was further pressurised to 20 bar (2,000 $kP_a$). The ethylene oxide was then pumped into the reactor at a rate of 6.0 g/min until 33.0 g (0.756 mmol) was present. The reactor content was maintained at the above temperature and pressure (by the continuous supply of $CO_2$). After 4.5 hours the temperature was increased to 120° C. and the reactor content was maintained at this temperature and at 20 bar (excess $CO_2$ was released via a back pressure regulator). Samples were taken at regular time intervals and analysed by gas liquid chromatography (GLC). The results of these Examples are shown in Table 1.

Catalyst 4 (Comparative) TBPMI/$K_2CO_3$

The reactor was filled with water (22.67), TBPMI (2.81 g, 8.14 mmol) and $K_2CO_3$ (0.30 g, 2.20 mmol). The reactor was then purged with $CO_2$ and pressurised with a $CO_2$ atmosphere of approximately 5 bar (500 kPa). The reactor content was then heated to 90° C. and the reactor was further pressurised to 20 bar (2,000 kPa). The ethylene oxide was then pumped into the reactor at a rate of 6.0 g/min until 33.0 g (0.756 mmol)

was present. The reactor content was maintained at the above temperature and pressure (by the continuous supply of $CO_2$). After 4.5 hours the temperature was increased to 120° C. and the reactor content was maintained at this temperature and at 20 bar (excess $CO_2$ was released via a back pressure regulator). Samples were taken at regular time intervals and analysed by gas liquid chromatography (GLC). The results of this Example are shown in Table 1.

TABLE 1

| | Carboxylation | | | | Hydrolysis 120° C. | |
|---|---|---|---|---|---|---|
| Catalyst | EO conv % (t = 30 min) | Selectivity % (t = 30 min) | | | TOF $h^{-1}$ (EC/MEG) | EC conv t = 60 min | TOF $h^{-1}$ (MEG) |
| | | EC | MEG | Total | | | |
| 1 | 74 | 92.5 | 7.3 | 99.8 | 136 | 38 | 101 |
| 2 | 84 | 94.5 | 5.4 | 99.9 | 154 | 23 | 63 |
| 3 | 71 | 98.1 | 1.8 | 99.9 | 139 | 17 | 49 |
| 4 | 86 | 94.4 | 5.5 | 99.9 | 159 | 39 | 104 |

Catalyst 5

TMG-iodide/TMG-molybdate 1,1,3,3-tetramethylguanidine (1.21 g, 10.5 mmol) was dissolved in water (32.8 g). $MoO_3$ (0.225 g, 1.58 mmol) and hydroiodic acid (1.65 g, 7.35 mmol, 57 wt % solution in water) were slowly added to this solution. This yielded a solution of 1,1,3,3-tetramethylguanidine iodide and 1,1,3,3-tetramethylguanidine molybdate with concentrations of 0.22M and 0.094M, respectively.

The reactor was filled with the catalyst composition in water, prepared as stated above. The reactor was then purged with $CO_2$ and pressurised with a $CO_2$ atmosphere of approximately 5 bar (500 kPa). The reactor content was then heated to 90° C. and the reactor was further pressurised to 20 bar (2,000 kPa). The ethylene oxide was then pumped into the reactor at a rate of 6.0 g/min until 33.0 g (0.756 mmol) was present. The reactor content was maintained at the above temperature and pressure (by the continuous supply of $CO_2$ and by release of excess $CO_2$ via a back pressure regulator). Samples were taken at regular time intervals and analysed by gas liquid chromatography (GLC). The results of these Examples are shown in Table 2.

TABLE 2

| Catalyst | EO conv % | Selectivity % (t = 30 min) | | | TOF $h^{-1}$ (MEG) |
|---|---|---|---|---|---|
| | | EC | MEG | Total | |
| 5 | 90.9 | 0.5 | 97.2 | 97.7 | 67 |

The catalysts of the present invention demonstrate high levels of selectivity and activity in both the carboxylation of ethylene oxide and the subsequent hydrolysis of the resultant ethylene carbonate to monoethylene glycol. The catalysts can also be used successfully in a heterogeneous system allowing facile separation of the product monoethylene glycol from the catalyst. Catalyst 3 demonstrates a heterogeneous system showing increased conversion and a reduced reaction time for the complete conversion of ethylene oxide to monoethylene glycol when compared to comparative catalyst 4.

What is claimed is:

1. A process for the conversion of an alkylene oxide to the corresponding alkylene glycol in the presence of carbon dioxide, water and a catalytic composition comprising a mixture of an organic base present in an amount in the range of from 10 to 90 mol % (based on the mixture) and a salt of the organic base and a hydrogen halide the salt being present in an amount in the range of from 10 to 90 mol % (based on the mixture), wherein the organic base comprises a carbon-based compound comprising one or more nitrogen atoms with at least one free electron pair and/or one or more phosphorous atoms with at least one free electron pair, and has a pKa high enough that it is capable of binding carbon dioxide under the reaction conditions.

2. The process as claimed in claim 1, wherein the catalytic composition is immobilised on a solid support.

3. The process as claimed in claim 2, wherein the solid support comprises a polymeric backbone.

4. The process as claimed in claim 1, wherein the organic base has a pKa of at least 8.

5. The process as claimed in claim 1, wherein the organic base has a pKa of at least 13.

6. The process as claimed in claim 1, wherein the organic base is selected from the group consisting of amines, hydroxylamines, hydrazines, hydrazones, amidines, amidrazones, hydrazidines, formazans, carbodiimides, guanidines, ureas, cyanamides, pyridines, pyrimidines, quinolines, imidazoles, triazoles, phosphazenes, phosphines, imines, and imides.

7. The process as claimed in claim 1, wherein the organic base is selected from the group consisting of amines, phosphazines, pyridines, and guanidines.

8. The process as claimed in claim 1, wherein the hydrogen halide is selected from the group consisting of hydrogen fluoride, hydrogen chloride, hydrogen bromide, and hydrogen iodide.

9. The process as claimed in claim 1, wherein the hydrogen halide is hydrogen iodide.

10. The process as claimed in claim 1, wherein water is present in an amount in the range of from 0.2 to 25 mol/mol alkylene oxide present in the reaction mixture.

11. The process as claimed in claim 1, wherein water is present in an amount in the range of from 1 to 5 mol/mol alkylene oxide present in the reaction mixture.

12. The process as claimed in claim 1, wherein the free organic base present in the catalytic composition is further reacted with molybdic acid.

13. The process as claimed in claim 1, wherein the total amount of carbon dioxide supplied to the reactor is in an amount in the range of from 0.5 to 100 mol/mol alkylene oxide.

14. The process as claimed in claim 1, wherein the total amount of carbon dioxide supplied to the reactor is in an amount in the range of from 0.5 to 10 mol/mol alkylene oxide.

15. The process as claimed in claim 1, wherein the alkylene oxide is ethylene oxide.

16. A process for the conversion of ethylene oxide to ethylene glycol in the presence of carbon dioxide, water and a catalytic composition comprising a mixture of an organic base present in an amount in the range of from 10 to 90 mol % (based on the mixture) and a salt of the organic base and hydrogen iodide the salt being present in an amount in the range of from 10 to 90 mol % (based on the mixture), wherein the organic base is selected from the group consisting of amines, phosphazines, pyridines, and guanidines, and wherein the organic base has a pKa of at least 8.

17. The process as claimed in claim 16, wherein water is present in an amount in the range of from 1 to 5 mol/mol ethylene oxide present in the reaction mixture.

18. The process as claimed in claim 16, wherein water is present in an amount in the range of from 1 to 1.3 mol/mol ethylene oxide present in the reaction mixture.

19. The process as claimed in claim 16, wherein the total amount of carbon dioxide supplied to the reactor is in an amount in the range of from 0.5 to 10 mol/mol ethylene oxide.

20. The process as claimed in claim 16, wherein the catalytic composition is immobilised on a solid support which comprises a polymeric backbone.

* * * * *